United States Patent [19]

Hensens et al.

[11] Patent Number: 4,952,604

[45] Date of Patent: Aug. 28, 1990

[54] ANTIFUNGAL AGENT

[75] Inventors: Otto D. Hensens, Red Bank; Jerrold M. Liesch, Princeton Junction; James A. Milligan, Plainsboro, all of N.J.; Sagrario M. Del Val, Madrid, Spain; Robert E. Schwartz; Carol Wichmann, both of Westfield, N.J.

[73] Assignee: Merck & Co., Inc., Rahway, N.J.

[21] Appl. No.: 346,768

[22] Filed: May 3, 1989

[51] Int. Cl.$^5$ .................... A61K 31/35; C07D 309/10
[52] U.S. Cl. ...................................... 514/459; 549/417
[58] Field of Search ........................ 549/417; 514/459

[56] References Cited

U.S. PATENT DOCUMENTS 4,389,410  6/1983  O'Hanlon ............................ 549/417

Primary Examiner—Nicky Chan
Attorney, Agent, or Firm—Alice O. Robertson; Charles M. Caruso

[57] ABSTRACT

Pyranyl ester compounds isolated from the fermentation of the species Penicillium are described. The compounds are useful as antifungal agents.

6 Claims, 2 Drawing Sheets

ANTIFUNGAL AGENT

The present invention is concerned with pryanyl ester antifungal antibiotic agent produced by the cultivation of the species Penicillium and to compositions containing said agent. By "antibiotic" agent as herein employed is meant compounds having chemotherapeutic properties produced by microorganisms and is not limited to antibacterial agents as the term is sometimes employed.

DESCRIPTION OF THE INVENTION

According to the invention it has been discovered that a fermentation product having broad antifungal properties may be obtained by the controlled cultivation of a previously undescribed microorganism isolated from soil and belonging to the genus Penicillium.

The antibiotic fermentation product may be represented generically by the formula (I):

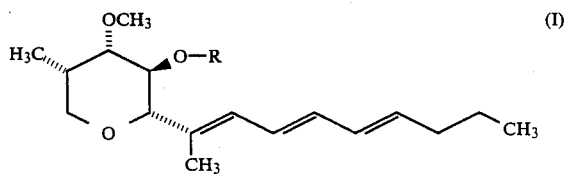

wherein R is —COCH$_2$NH$_2$ or —COCH$_2$N(CH$_3$)$_2$.

The components are represented by the following names and structures:

(1) (2α,3β,4α,5α)-tetrahydro-4 methoxy-5-methyl-2(1-methyl 1,3,5-nonatrienyl)-2H-pyran-3 -yl L-glycine represented by the formula (I A):

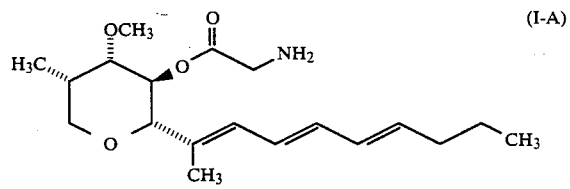

and (2) (2α,3β,4α,5α)-tetrahydro-4-methoxy-5-methyl-2-(1-methyl-1,3,5 nonatrienyl)-2H-pyran-3-yl N,N-dimethyl-L-glycine (I-B):

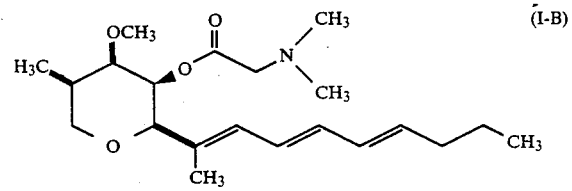

The structures of the component compounds of the antifungal antibiotic of the present invention have been determined by detailed analyses of the various spectral characteristics of the compounds.

Mass Spectral Data

Spectra were recorded on a Finnigan-MAT MAT212 mass spectrometer in the electron impact mode (EI, 90 eV). Exact mass measurements were performed using the peak matching method with perfluorokerosene as internal standard. From the data, the molecular formulas were determined as follows:

| Compound | Molecular Formula | Molecular Weight Calcd | Molecular Weight Found |
|---|---|---|---|
| IA | C$_{19}$H$_{31}$NO$_4$ | 337.2253 | 337.2251 |
| IB | C$_{21}$H$_{35}$NO$_4$ | 365.2566 | 365.2558 |

NMR Spectral Data

Figure 1:
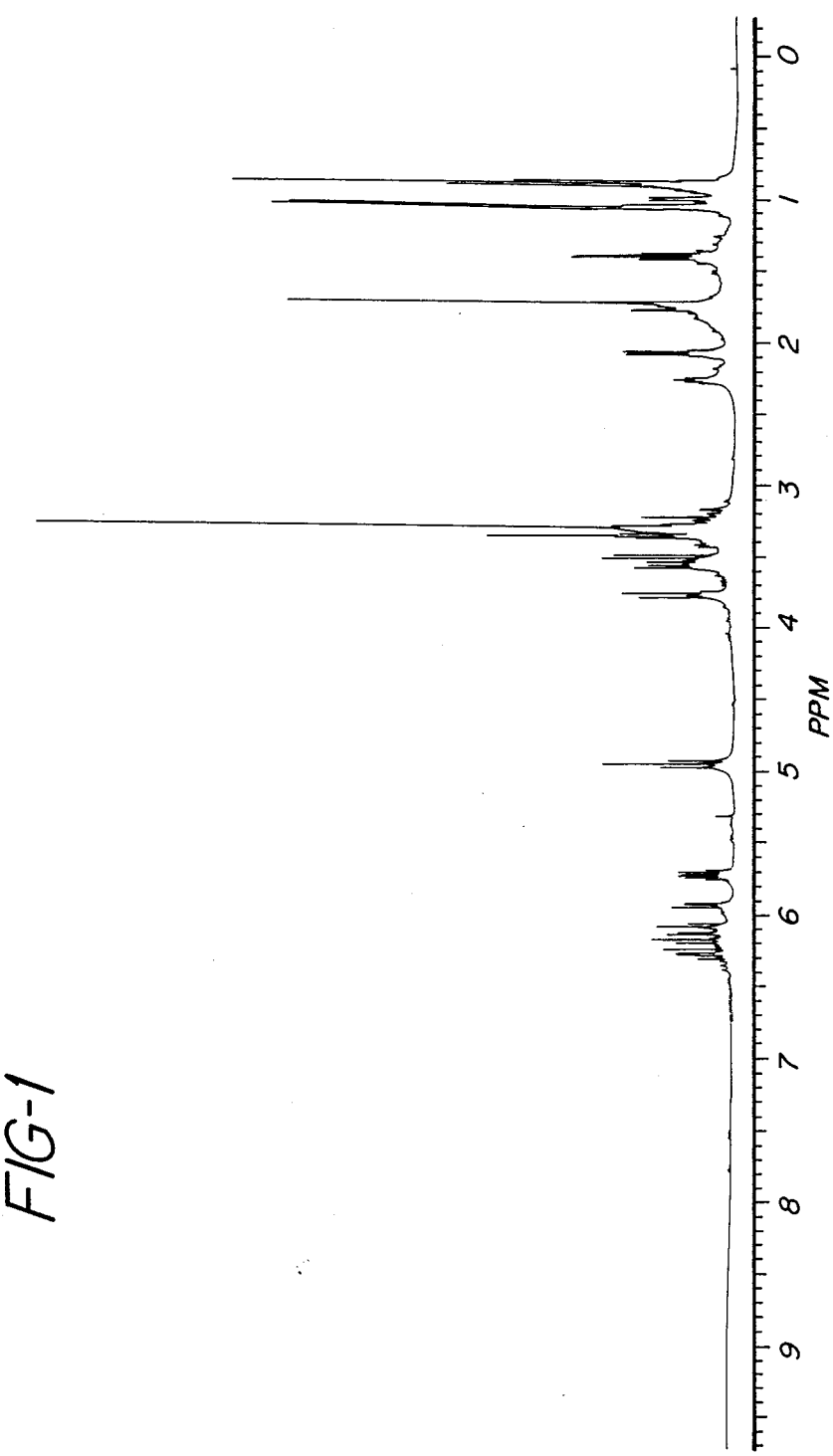
Figure 2:
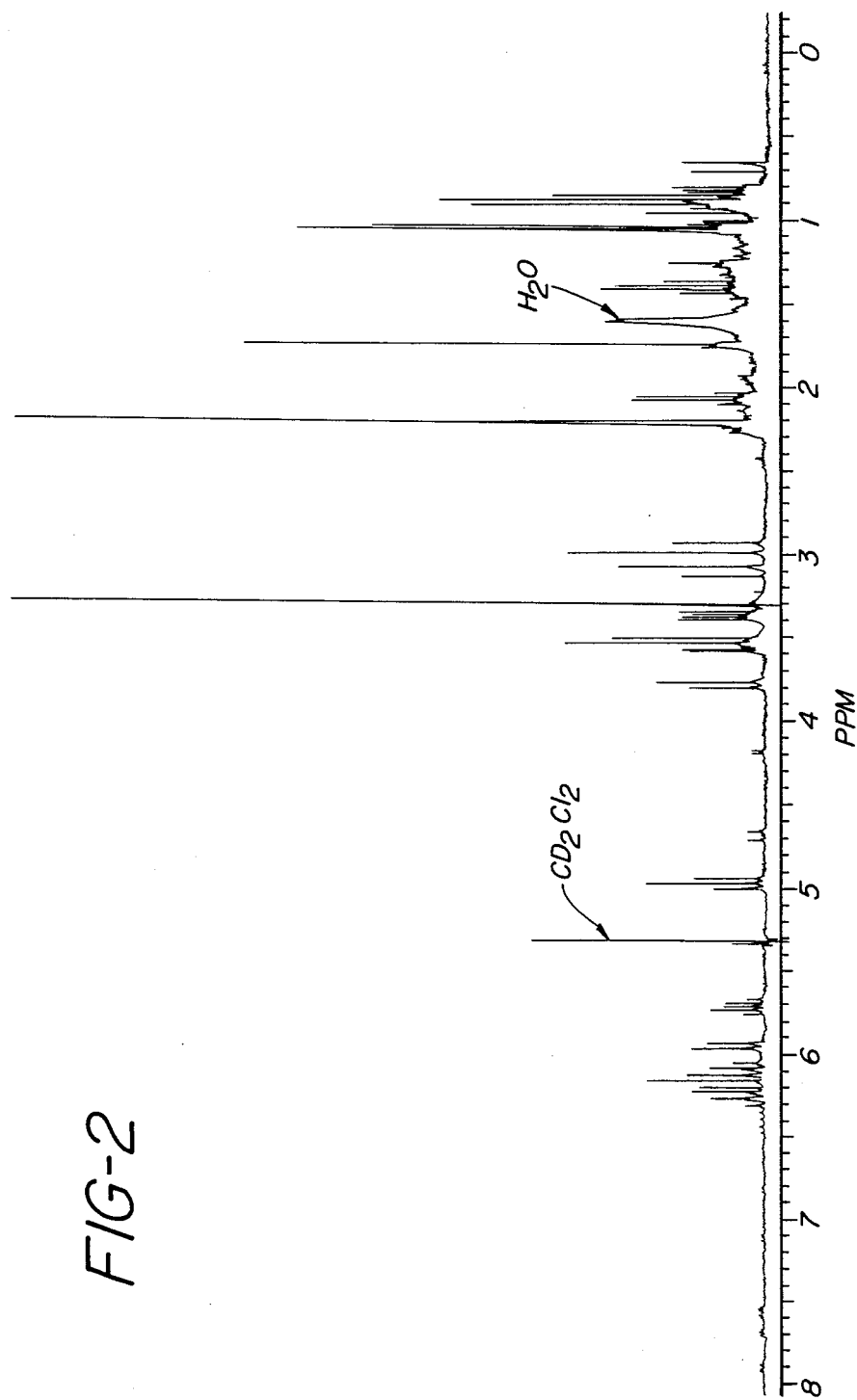

The $^1$H NMR spectra were recorded at ambient temperature in CD$_2$Cl$_2$ on Varian XL 300 and XL 400 NMR spectrometers. Chemical shifts are shown in ppm relative to tetramethylsilane (TMS) at zero ppm using solvent peak at 5.32 ppm internal standard as seen in accompanying figures:
Compound IA: FIG. 1
Compound IB: FIG. 2

The $^{13}$C NMR spectra were recorded in CD$_2$Cl$_2$ at ambient temperature on Varian XL 300 and XL 400 NMR spectrometers. Chemical shifts are given in ppm relative to tetramethylsilane (TMS) at zero ppm using the solvent peak at 53.8 ppm as internal standard.

Compound IA: (100 MHz) 10.9, 11.9, 13.8, 22.8., 32.8, 35.3, 44.3, 56.5, 69.5, 71.1, 81.9, 85.7, 126.2, 129.6, 131.0, 133.7, 134.3, 136.1, 173.9 ppm.

Compound IB: (75 MHz) 10.9, 11.9, 13.8, 22.8, 32.8, 35.2, 45.0, 56.5, 60.6 (2x), 69.1, 71.1, 81.9, 85.7, 126.3, 129.8, 131.0, 133.6, 134.3, 135.9, 169.9 ppm.

UV Spectral Data

UV spectrum in methanol showed following maxima:
Compound IA
  286 nm (E % 849)
  275 nm (E % 1079)
  E265 nm (E % 829)
Compound IB
  287 nm (E % 1089)
  275 nm (E % 1388)
  266 nm (E % 1063)
  205 nm (E % 1696)

IR Spectral Data

Compound IA 1747 cm$^{-1}$
Compound IB 1750 cm$^{-1}$

On the bases of these and other data, Compounds IA-IB are believed with considerable certainty to have the structures indicated.

The compounds are white or light colored solids soluble in organic solvents. Thus, they are adaptable to be employed in solution. They are also adaptable to be employed in aqueous dispersions.

Compound IA is the major component and is the preferred compound.

The compounds of this invention have antifungal properties against both yeasts and filamentous fungi. They are particularly useful against organisms causing pathogenic mycotic infections such as *Candida albicans. Candida rugosa* and the like. However, they may be employed to control not only growth of fungi causing mycotic infections in human and animal species, but also fungi which attack plants, plant and wood products or articles of commerce.

Among the filamentous fungi against which compounds are useful are *Ceratocystis ulmi, Rhizomucor miehei,* and *Ustilago zeae.* Among the yeasts are the aforementioned *Candida albicans* and *Candida rugosa* and also *Candida tropicalis.* The compounds are also active against certain bacteria such as Streptomyces species. Some others of the specific fungi and yeasts which may be controlled include *Botrytis allii, Cochliobolus miyabeanus, Penicillium* sp., *Trichoderma lignorum. Trichoderma* sp., *Candida tronicalis,* and *Saccharomyces cerevisiae.*

The antifungal compounds of the present invention, Compound I, are conveniently produced by cultivating a previously unknown strain of the microorganism, *Penicillium restrictum,* isolated from soil and designated MF 5261 in the culture collection of Merck & Co., Rahway, N.J. and recovering said compound from the culture. A sample of the culture capable of producing the compound has been deposited under the Budapest Treaty in the culture collection of the American Type Culture Collection, 12301 Parklawn Drive, Rockville, Md. 20852. The sample has been assigned the accession number ATCC 20927.

The colonial and morphological description of MF 5261, ATCC 20927 are set forth below:

A. Colonial description

Colonies (one week old) on Czapek yeast extract agar, effuse, 20 mm in diameter, with predominantely floccose aerial mycelium, up to 1 mm deep, plane to sulcate in side view, surface white to pale grayish buff, reverse tan, grayish tan, buff to pale cream at the margin, without soluble pigments or exudates.

B. Morphological description

Conidiophores micronematous to semi-macronematous, monoverticilliate, without rami or metulae, unbranched, aspetate, straight to slightly curved, 15-28-×2-4 μm, with non-inflated to slightly inflated apices, arising directly from aerial mycelium. Phialides arising directly from conidiophore apices, ampulliform to cylindrical, tapered to a truncate apex, 5.5-8×2.5-3 μm, usually 3-5/conidiophore, but ranging from 1 to 8.

Conidia globose to subglose, 3 3.5 μm in diameter, hyaline, smooth to faintly punctate, occasionally with faint traces of disjunctors, adhering to conidiophores in dry chains.

The culture was identified according to the method of J. I. Pitt described in "The genus Penicillium and its teleomorphic states Eurenicillium and Talaromyces." Academic Press, London, 1979 and found that it agrees well with the description of *Penicillium restrictum.*

Although the invention is discussed hereinbelow principally with respect to the specific strain, it is well-known in the art that the properties of microorganisms may be varied naturally and artificially. Thus, all strains of the genus ATCC 20927 including varieties and mutants, whether obtained by natural selection, produced by the action of mutating agents such as ionizing radiation or ultraviolet irradiation, or by the action of chemical mutagens such as nitrosoguanidine, are contemplated to be within the scope of this invention.

The fermentation is carried out in a medium containing sources of carbon and nitrogen assimilable by the microorganism and also containing low levels of inorganic salts. In addition, the medium may be supplemented with trace metals, although if complex sources of carbon and nitrogen are employed, the trace metals are usually present in the sources.

The sources of carbon include glycerol, sugars, starches and other carbohydrates, or carbohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 5 percent by weight of the medium is satisfactory. These carbon sources can be used individually or several such carbon sources may be combined in the same medium.

The sources of nitrogen include amino acids such as glycine, arginine, threonine, methionine and the like as well as complex sources such as yeast hydrolysates, yeast autolysates, yeast cells, tomato paste, soybean meal, casein hydrolysates, yeast extracts, corn steep liquors, distillers solubles, cottonseed meal, meat extract, and the like. The various sources of nitrogen can be used alone or in combination in amounts ranging from 0.2 to 90 percent by weight of the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalt, manganese, iron, molybdenum, zinc, cadmium, and the like.

Other media suitable for growing strains of *Penicillium restrictum,* ATTC 20927, are described below. These, however, are merely illustrative of the wide variety of media which may be employed and are not intended to be limiting.

| Medium A | |
|---|---|
| Dextrose | 1.0 g. |
| Soluble starch | 10.0 g. |
| Beef extract | 3.0 g. |
| Yeast autolysate (as ardamine PH available from Yeast Products Inc., Clifton, N.J.) | 5.0 g. |
| NZ Amine-E (casein hydrolysate-available from Humko-Sheffield-Memphis, Tenn) | 5.0 g. |
| $MgSO_4.7H_2O$ | 0.05 g. |
| Phosphate Buffer | 2.0 ml. |
| $CaCO_3$ | 0.5 g. |
| Distilled water | to 1000 ml. |
| pH | 7.0-7.2 |
| Phosphate Buffer | |
| $KH_2PO_4$ | 91.0 g. |
| $Na_2HPO_4$ | 95.0 g. |
| Distilled water | to 1000 ml. |
| pH | 7.0 |

| Medium B | |
|---|---|
| Tomato paste | 20.0 g. |
| Primary yeast | 10.0 g. |
| Dextran (CPC starch) | 20.0 g. |
| $CoCl_2.6H_2O$ | 0.005 g. |
| Distilled water | to 1000 ml. |
| pH | 7.2-7.4 |

| Medium C | |
|---|---|
| Corn meal | 20.0 g. |
| Distillers solubles | 10.0 g. |
| Soybean meal | 15.0 g. |
| Sodium citrate | 4.0 g. |
| $CaCl_2.2H_2O$ | 0.5 g. |
| $MgSO_4.7H_2O$ | 0.1 g. |
| $CoCl_2.6H_2O$ | 0.01 g |
| $FeSO_4.2H_2O$ | 0.01 g |
| Polyglycol P2000 (Polypropylene glycol mw 2000) | 2.5 ml. |
| Distilled water | to 1000 ml. |

-continued

| Medium C | |
|---|---|
| pH | 6.5 |

| Medium D | |
|---|---|
| Lactose | 20.0 g. |
| Distillers solubles | 15.0 g. |
| Autolyzed yeast (Ardamine PH) | 5.0 g. |
| Distilled water | to 1000 ml. |
| pH | 7.0 |

| Medium E | |
|---|---|
| Tomato paste | 40.0 g. |
| Oat flour | 10.0 g. |
| Distilled water | to 1000 ml. |
| pH | 7.0 |

| Medium F | |
|---|---|
| Corn Steep Liquor | 15.0 g. |
| $(NH_4)_2SO_4$ | 4.0 g. |
| $CaCO_3$ | 6.0 g. |
| Soluble Starch | 20.0 g. |
| Corn meal | 1.0 g. |
| Soybean meal | 4.0 g. |
| Glucose | 5.0 g. |
| $KH_2PO_4$ | 0.3 g. |
| Lard water | 2.5 g. |
| Distilled water | to 1000 ml. |
| pH | 6.7 |

| Medium G | |
|---|---|
| Dextrose | 10.0 g. |
| Asparagine | 1.0 g. |
| $K_2HPO_4$ | 0.1 g. |
| $MgSO_4.7H_2O$ | 0.5 g. |
| Yeast Extract | 0.5 g. |
| Oat Flour | 10.0 g. |
| $CaCO_3$ | 3.0 g. |
| Trace Element Mix | 10.0 ml. |
| Distilled water | to 1000 ml. |
| Adjust pH to | 7.2 |

| Trace Element Mix | |
|---|---|
| $FeSO_4.7H_2O$ | 1000 mg. |
| $MnSO_4.4H_2O$ | 1000 mg. |
| $CuCl_2.2H_2O$ | 25 mg. |
| $CaCl_2.2H_2O$ | 100 mg. |
| $H_3BO_3$ | 56 mg. |
| $(NH_4)_6Mo_4O_{24}.6H_2O$ | 19 mg. |
| $ZnSO_4.7H_2O$ | 200 mg. |
| Distilled water | to 1000 ml. |

| Medium H | |
|---|---|
| Medium G | 1000 ml. |
| Oat Flour | 10 g. |
| pH | 7.2 |

In the preferred process for producing Compound I, a fermentation broth containing *Penicillium restrictum.* ATCC 20927 is prepared by inoculating spores or mycelia of the antibiotic-producing organism into a suitable medium and then cultivating under aerobic conditions.

The procedure generally is first to inoculate a preserved source of culture into a nutrient seed medium and to obtain, preferably through a two step procedure, growth of the organisms which serve as seeds in the production of the antifungal agent. Representative seed media are those having the compositions:

| Seed Medium - HL | |
|---|---|
| $KH_2PO_4$ | 15 g |
| Cerelose | 20 g |
| Ardamine PH | 1 g |
| Pharmamedia | 15 g |
| Lactic Acid (85%) | 2 ml |
| Trace Elements Mix | 10 ml. |
| pH | 7.0 |

| Trace Elements Mix: | |
|---|---|
| $FeSO_4.7H_2O$ | 1 g |
| $MnSO_4.4H_2O$ | 1 g |
| $CuCl_2.2H_2O$ | 25 mg |
| $CaCl_2$ | 100 mg |
| $H_3BO_3$ | 56 mg |
| $(NH_4)_6Mo_4O_2.4H_2O$ | 19 mg |
| $ZnSO_4.7H_2O$ | 200 mg |
| Distilled Water | to 1000 ml |

| Seed Medium - KF | |
|---|---|
| Corn Steep Liquor | 5 g |
| Tomato Paste | 40 g |
| Oat Flour | 10 g |
| Glucose | 10 g |
| Trace Element Mix | 10 ml |
| Distilled Water | to 1000 ml |
| pH | 6.8 |

In the production of the compound, a slant section of a preserved culture of MF 5261, ATCC 20927 is inoculated into an appropriate nutrient seed medium of pH in the range 5 to 8.1, optimally 6 to 7.5, and the flask incubated with or without agitation at temperatures in the range of from about 15° C. to about 30° C., preferably 20° to 28° C. Agitation when employed, may be up to 400 rpm, preferably, about 200 to 220 rpm. The incubation is carried out over a period of from 2 to 30 days, preferably 2 to 14 days. When growth is abundant, usually between 2 and 5 days, the culture growth may be used to inoculate the production medium for the production of the antifungal agent. Preferably however, a second stage fermentation is carried out, inoculating with a portion of the culture growth and then employing similar conditions but generally with a shortened incubation period of about 1 to 3 days. The growth from the second stage then is employed to inoculate the production medium.

Fermentation production media are then inoculated with the culture growth. Preferred production media are solid growth media. Representative media are represented by the following of which Medium I is preferred.

Medium I 10 grams of cracked corn per flask together with 15 milliliters of F-108 Medium of the following composition:

| Yeast extract | 3.3 g |
|---|---|
| Na tartrate | 6.7 g |
| $FeSO_4.7H_2O$ | 0.7 g |
| Distilled Water | to 1000 ml |

Medium II 3.0 grams of vermiculite per flask together with 30 milliliters of F-LM Medium of the following composition:

| Dextrose | 20.0 g |
|---|---|
| Glycerol | 20.0 g |
| Ardamine PH | 10.0 g |
| $CoCl_2.6H_2O$ | 8 mg |
| Polyglycol P-2000 | 2.5 ml. |
| $CaCO_3$ | 16.7 g |
| Na tartrate | 3.3 g |
| Distilled Water | to 1000 ml |

The fermentation production medium, inoculated with the culture growth, is incubated for 3 to 30 days, usually 7 to 14 days preferably with, but also without agitation. The fermentation may be conducted aerobically at temperatures ranging from about 20° C. to about 40° C. Airflow may be from 2.0 to 5.0 liters per minute and agitation may be at a rate of 200 to 500 rpm. For optimum results, it is most convenient to conduct these fermentations at a temperature in the range of from about 24° C. to about 30° C. Temperatures of about 24°–28° C. are preferable. The pH of the nutrient medium suitable for producing the instant compounds can vary from about 5.0 to 8.5 with a preferred range of from about 6.0 to 7.5. After the appropriate period for the production of the desired compound, the latter is recovered from the fermentation medium as hereinafter described.

The active material may be recovered from the solid fermentation medium by steps comprising adding methanol to extract the solid substrate, stirring to complete the extraction into the methanol, and then filtering to recover the methanol solution as filtrate.

The methanol filtrate is diluted with water and then partitioned with an equal volume of a non polar solvent such as methylene chloride. The non-polar solvent extract is concentrated under vacuum and if not immediately used is stored at −80° C., to slow decomposition.

The extract then may be further concentrated, reconstituted with ethyl acetate/hexane and chromatographed on silica gel using step gradient chromatography with ethyl acetate/hexane and ethyl acetate/methanol as solvents and monitoring the elution for active agent with *Candida albicans*. The active eluant fractions are concentrated and chromatographed via preparative HPLC to obtain the desired product.

The antifungal activity of the compounds may be detected in an antifungal assay employing disc diffusion methods against a panel of representative yeasts, filamentous fungi (molds) and bacteria.

For carrying out the assay, seeded assay plates are prepared in the following manner according to the type of assay strain.

Inocula for filamentous fungi are prepared by scraping the surface of stock plates maintained on potato dextrose agar with a moistened sterile dacron swab. The spores and mycelia are then suspended in 10 milliliters of sterile potato dextrose broth and adjusted to 70 percent transmission at 660 nm.

Inocula for yeasts and bacterial strains are prepared from overnight broth cultures then diluted into potato dextrose agar to a final concentration of either 40 percent or 70 percent transmission at 660 nm.

For strains of *Candida albicans* and *Saccharomyces cerevisiae*, sterile saline is employed in place of potato dextrose broth. Assay plates are prepared by diluting the inoculum into appropriate molten agar medium, cooled to 45° C. to obtain a final concentration of 4 percent.

Seeded agar for Streptomyces sp. is prepared from a commercially available spore suspension which is diluted directly into molten agar (45° C.) to obtain a final concentration of 0.1 percent.

The seeded agar media thus prepared are dispensed into Petri dishes for assays (11 milliliters per dish).

The samples to be tested for production of antifungal agent are applied to 6.2 mm. filter paper discs (25 microliter/disc) and air dried at 24° C. When the sample to be tested is crude broth, it may be centrifuged prior to application. The discs bearing the material to be tested are then applied employing sterile conditions to the seeded assay plates and the samples rewet with 25 percent sterile aqueous dimethylsulfoxide (25 μl/disc). The assay plates are then incubated at either 28° C. or 37° C. for 24 hours.

Following incubation, the inhibition zones are measured and recorded. The measurements are made from the extreme edge where growth differs from the background zone. The growths are noted as to appearance as fuzzy edge and clear center, hazy throughout, slightly hazy, very hazy or ringed.

The products of the present invention demonstrated a broad spectrum of antifungal activity in the foregoing tests. Particularly wide inhibition zone were noted with *Candida albicans, Candida rugosa, Ceratocystis ulmi, Rhizomucor miehei*, and *Ustilago zeae*.

In view of the broad spectrum of activity, the products of the present invention either singly or as a mixture are adaptable to being utilized in various applications of antifungal compositions. In such use, compounds may be admixed with a biologically inert carrier, generally with aid of a surface active dispersing agent, the nature of which would vary depending on whether the use is for the control of pathogens infecting man or animals, or for control of fungi in agriculture such as in soil or plant parts, or for the control of fungi in inanimate objects.

In compositions for medical applications, the compounds may be admixed with a pharmaceutically acceptable carrier, the nature of which will vary depending on whether the composition is to be topical, parenteral or oral.

If said application is to be topical, the drug may be formulated in conventional creams and ointments such as white petrolatum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the usual pharmaceutical media, including, for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of a compound of Formula I. The appropriate doses will vary depending on age, severity, body weight and other conditions. For topical application the compositions are applied directly to the area where control is desired. For internal administration, the composition may be applied by injection or may be administered orally.

For non-medical application, the product of the present invention, either singly or as a mixture, may be employed in compositions in an inert carrier which includes finely divided dry or liquid diluents, extenders, fillers, conditioners and excipients, including various clays, diatomaceous earth, talc, and the like, or water and various organic liquids such a lower alkanols, for example ethanol and isopropanol, or kerosene, benzene, toluene and other petroleum distillate fractions or mixtures thereof.

These compositions may be employed by applying to the surface of or incorporating in the medium to be protected. For the control of rice blast, tomato late blight, tomato early blight, wheat leaf rust, bean powdery mildew and tomato Fusarium wilt, the compositions may be applied directly to the plant in topical application or administered to the soil for systemic application. The method comprises administering to the affected plant, soil or medium to be protected an antifungally effective amount of the compound of Formula I.

The following example illustrates the invention but is not to be construed as limiting:

EXAMPLE I

A culture, identified as 8642 301F, and received as a soil tube was fermented in solid substrate medium of contents of above-described Medium I. Initially, seed media KF and HL were inoculated with one glass scoop of soil from the soil tube and incubated for 48 and 72 hours at 26° C. and 85% humidity, and agitation at 220 rpm. Two milliliter aliquots of the seed media were then aseptically transferred into multiple production flasks of production Medium I and incubated at 26° C. and 85% humidity with agitation at 220 rpm. After 7 or 14 days, the production flasks were harvested by extracting the contents of the flasks with 30 milliliters of 70 percent methanol, after manually breaking the mycelial growth and subsequently agitating the flasks for 60 minutes at 220 rpm to obtain a fermentation product in the extracts.

Samples of the extracts were subjected to antifungal determination. Samples of the extracts were tested for activity against *Candida albicans* MY 1208 in a standard disc diffusion assay on plates seeded with said organisms. All plates showed reduction of growth when compared with control plates.

EXAMPLE II $2\alpha,3\beta,4\alpha,5\alpha$-Tetrahydro-4-methoxy
5-methyl-2-(1-methyl-1,3,5-nonatrienyl) 2H-pyran
3-yl-L-glycine (Compound IA)

A. Fermentation

The contents one vial (containing approximately 2 mL frozen vegetative mycelial cells of Merck Culture 8642-301F) were inoculated into a 250 mL plain Erlenmeyer flask containing 50 mL of the following media: corn steep liquor, 5 g; tomato paste, 40 g; oat flour, 10 g; glucose, 10 g; and trace elements mix, 10 ml (of the same composition as trace element mix of Seed Medium HL) in one liter of distilled water. The pH of the medium was adjusted to 6.8 and the mixture autoclaved for 20 minutes at 121° C. prior to inoculation. The culture was incubated at 27 with rotary agitation at 220 RPM for 72 hours. Ten mL of this culture were used to inoculate a second stage seed flask (containing 500 mL of the same seed medium). The second stage seed was cultivated at 27° C. with rotary agitation at 200 RPM for 48 hours.

The production media (in 6.5 mm × 13 mm × 43 mm plastic trays with lids) consisted of the following: cracked corn, 480 g; and nurient solution, 720 mL (of composition: yeast extract, 33.3 g; sodium tartrate, 6.7 g; $FeSO_4 \cdot 7H_2O$, 0.67 g in 1 liter distilled water). The medium was autoclaved for 20 minutes at 121° C., followed by the addition of 500 mL water and a second autoclaving for 20 minutes at 121° C.

Thereafter, the trays were allowed to cool and each tray was inoculated with 50 mL of the seed culture, the contents mixed with a sterile spatula, and covered and incubated at 26° for 14 days without agitation.

B. Isolation

The contents of ten trays of solid fermentation medium (equivalent to 20 liters of liquid fermentation medium) were extracted with a total of 20 liters of methanol by stirring the suspension for 10 to 15 minutes and thereafter filtering under reduced pressure to obtain a filtrate which amounted to 14 liters and contained 237 grams of solid. It was diluted with 4.2 liters of water and partitioned with 14 liters of methylene chloride. On separation, the methylene chloride solution amounted to 12 liters; the latter was dried over sodium sulfate and then filtered. The 12 liter extract was concentrated under vacuum to 1.44 liters. The concentrate contained 4.7 grams of total solids and was stored at −80° C. where it underwent slow decomposition.

Thirty milliliters of the concentrate was first concentrated to dryness, reconstituted to 4 milliliters with ethyl acetate/hexane (75/25) and chromatographed on 200 milliliters of silica gel (Kieselgel 60, 0.040–0.063 mm) using a step gradient elution employing the following elutants: 75/25 ethyl acetate/hexane; ethyl acetate; 90/10 ethyl acetate/methanol; 80/20 ethyl acetate/methanol; 50/50 ethyl acetate/methanol; and methanol. The major activity was found in the eluate eluted with 90/10 ethyl acetate/methanol as determined by an assay which detects agents which inhibit *Candida albicans*. The eluate fraction showing major activity was concentrated to yield 15.1 milligrams. The activity rich cut was chromatographed employing preparative HPLC column (DuPont Zorbax $C_{18}$, 21.2 mm ID × 25 cm, 40° C. at 20 ml/min, methanol/0.01M potassium phosphate buffer (pH=7) 70/30, UV. 276 nm at 2.0 AUFS 0.05 mm pathlength cell) to obtain 4.5 mg of Compound IA. The UV spectrum (methanol) of this preparation showed maxima at 287 nm (E% 967), 275 nm (E% 1230) and 266 nm (E% 938). The IR spectrum showed strong absorbance at 1746 cm$^{-1}$.

A larger scale purification was carried out employing 500 milliliters of the 1.44 liter concentrate. In this purification, the concentrate was further concentrated to obtain 2.13 grams and the latter dissolved in 40 milliliters 75/25 of ethyl acetate/hexane. This solution was chromatographed on 1 liter of silica gel (E. Merck, 60–200 mesh, using the following elutants in a step-gradient elution: 75/25 ethyl acetate/hexane; ethyl acetate., 90/10 ethyl acetate/methanol; 80/20 ethyl acetate/methanol; and methanol). The major active components were again found in the 90/10 ethyl acetate/methanol eluate. This eluate cut was again chromatographed on 500 ml of silica gel (Kieselgel 60) employing step gradient elution with ethyl acetate; 95/5 ethyl acetate/methanol; and 90/10 ethyl acetate/methanol.

The eluate from ethyl acetate/methanol (90/10) cut was purified by preparative HPLC as above described to obtain 102 mg of (2α,3β,4α,5α)-tetrahydro-4-methoxy 5-methyl-2-(1-methyl-1.3,5-nonatrienyl)2H-pyran-3-yl L-glycine (Compound IA).

The product, although fairly stable was noted to undergo some decomposition in methanol. Forty milligrams of the product was further purified by step gradient chromatography on silica gel employing 50/50/2 ethyl acetate/hexane/ammonium hydroxide; 75/25/2 ethyl acetate/hexane/ammonium hydroxide; and 100/2 ethyl acetate/ammonium hydroxide. The active compound eluted with 100/2 ethyl acetate/ammonium hydroxide. The UV spectrum (MeOH) of the product showed maxima at 286 nm (E% 849), 275 nm (E% 1079) and 265 nm (E% 829); the IR showed strong absorbence at 1747 cm$^{-1}$.

EXAMPLE III (2α,3β,4α,5α) Tetrahydro 4-methoxy 5-methyl-2-(1-methyl 1,3,5-nonatrienyl) 2H-pyran-3-yl N,N-di-methyl-L-glycine (Compound IB)

Methylene chloride partitions were prepared from methanol extracts of four separate fermentations carried out as described in Example I. The partitions were combined and concentrated to obtain 10.2 grams of an oil.

The concentrate was dissolved in 300 milliliters of ethyl acetate/methanol (75:25) and chromatographed on a 6 liter silica gel column (E. Merck, 60 20 mesh) at 150 milliliter/minute using a step gradient elution with ethyl acetate/hexane (75:25) 8 liters; ethyl acetate (100) 4 liters; ethyl acetate/methanol (98:2) 4 liters; ethyl acetate/methanol (95:5) 4 liters; ethyl acetate/methanol (90:10) 8 liters; and methanol (100) 2 liters. The ethyl acetate/methanol (90:10) eluant was concentrated to recover Compound IA. The ethyl acetate, ethyl acetate/methanol (98:2) and ethyl acetate/methanol (95:5) eluants were combined and concentrated to obtain 3.1 grams of crude Compound IB.

The concentrate was taken up in 20 milliliters of ethyl acetate/hexane (1:1) to yield 15 milliliters of supernatant and 5 milliliters of precipitate. The supernatant was chromatographed on 500 milliliters of silica gel in a step gradient elution of ethyl acetate/hexane (1:1); ethyl acetate (100), ethyl acetate/methanol (90:10); and ethyl acetate/methanol (75:25).

The eluant/eluted with 100 percent ethyl acetate in the foregoing chromatographic separation were combined on the basis of biological activity and thin layer chromatography and concentrated to obtain 24 milligrams of residue. This concentrate was further purified on a 50 ml silica gel column employing step gradient elution using the same eluting agents as in the previous chromatographic separation. The fraction eluting with 100 percent ethyl acetate was concentrated to dryness to obtain 1.5 milligrams of purified (2α, 3β, 4α, 5α)-tetrahydro-4-methoxy-5-methyl 2-(1-methyl .1,3,5-nonatrienyl)-2H-pyran-3-yl N,N dimethyl-L glycine. The IR spectrum of this component contained an absorbance at 0.1750 cm$^{-1}$ and the UV spectrum in methanol contained $\lambda$max$'^S$ (E%) at 287 (1,089), 275 (1,388), 266 (1,063) and 205 (1,696).

What is claimed is:

1. A compound represented by the formula;

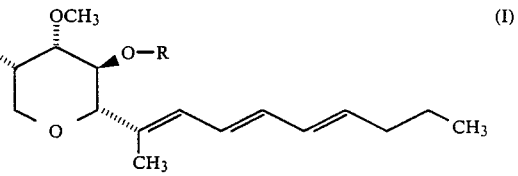

wherein R is COCH$_2$NH$_2$ or COCH$_2$N(CH$_3$)$_2$.

2. A compound according to claim 1 in which R is COCH$_2$NH$_2$.

3. A compound according to claim 1 in which R is COCH$_2$N(CH$_3$)$_2$.

4. An antifungal composition which comprises a compound of claim 1 or a mixture thereof in admixture with a biologically inert carrier.

5. A composition according to claim 1 in which the carrier is a pharmaceutically acceptable carrier.

6. A method for inhibiting fungal growth comprising applying to the area where growth is to be controlled, an antifungally effective amount of a compound of claim 1.

* * * * *